United States Patent
Li et al.

(10) Patent No.: US 12,025,496 B2
(45) Date of Patent: Jul. 2, 2024

(54) DRUG SCANNING AND IDENTIFICATION SYSTEM AND USE METHOD THEREOF

(71) Applicant: InnoSpectra Corporation, Hsin-Chu (TW)

(72) Inventors: Hsi-Pin Li, Hsin-Chu (TW); Fei-Peng Chang, Hsin-Chu (TW); He-Yi Hsieh, Hsin-Chu (TW); Pei-Ying Lin, Hsin-Chu (TW); Shu-Ping Chien, Hsin-Chu (TW); Yung-Yu Huang, Hsin-Chu (TW)

(73) Assignee: InnoSpectra Corporation, Hsin-Chu (TW)

( * ) Notice: Subject to any disclaimer, the term of this patent is extended or adjusted under 35 U.S.C. 154(b) by 0 days.

(21) Appl. No.: 17/964,926

(22) Filed: Oct. 13, 2022

(65) Prior Publication Data

US 2023/0124377 A1    Apr. 20, 2023

(30) Foreign Application Priority Data

Oct. 15, 2021    (CN) .......................... 202111206074.7

(51) Int. Cl.
  *G01J 3/26*    (2006.01)
  *G01J 3/28*    (2006.01)
  (Continued)

(52) U.S. Cl.
  CPC ............... *G01J 3/26* (2013.01); *G01J 3/2803* (2013.01); *G01J 3/42* (2013.01); *G01N 21/3563* (2013.01);
  (Continued)

(58) Field of Classification Search
  None
  See application file for complete search history.

(56) References Cited

U.S. PATENT DOCUMENTS

| | | |
|---|---|---|
| 9,665,689 B2 | 5/2017 | O'Brien et al. |
| 10,216,908 B2 | 2/2019 | O'Brien et al. |

(Continued)

FOREIGN PATENT DOCUMENTS

| | | |
|---|---|---|
| CN | 105651728 | 6/2016 |
| CN | 213148726 | 5/2021 |

(Continued)

OTHER PUBLICATIONS

"Office Action of Taiwan Counterpart Application", issued on Oct. 28, 2022, p. 1-p. 4.

(Continued)

*Primary Examiner* — Hina F Ayub
(74) *Attorney, Agent, or Firm* — JCIPRNET

(57) ABSTRACT

A drug scanning and identification system including a spectrometer, a drug holder, a mobile device and a drug identification model is provided. The spectrometer includes a light source, a diffraction grating, a light-absorption element, a wavelength selector, and a single-point photodetector. The drug holder includes a transparent area and a light-absorption area. The drug is disposed on the transparent area. The light-absorption area surrounds the transparent area. The mobile device is adapted to send a control command to trigger the spectrometer scanning the drug so as to obtain spectrum data of the drug. The spectrometer is adapted to transmit the spectrum data of the drug to the drug identification model. The drug identification model is adapted to identify the spectrum data of the drug such that the drug identification model generates an identification result. The identification result is displayed by the mobile device.

6 Claims, 8 Drawing Sheets

(51) Int. Cl.
*G01J 3/42* (2006.01)
*G01N 21/3563* (2014.01)
*G01N 21/359* (2014.01)
*G16H 20/10* (2018.01)
*G16H 40/63* (2018.01)

(52) U.S. Cl.
CPC ........... *G01N 21/359* (2013.01); *G16H 20/10* (2018.01); *G16H 40/63* (2018.01)

(56) References Cited

U.S. PATENT DOCUMENTS

| | | | |
|---|---|---|---|
| 10,790,052 B2 | 9/2020 | O'Brien et al. | |
| 2008/0174777 A1* | 7/2008 | Carron | G01N 21/718 356/300 |
| 2013/0293893 A1 | 11/2013 | Bonyuet et al. | |
| 2018/0172510 A1* | 6/2018 | Rosen | G01J 3/0205 |
| 2019/0026586 A1* | 1/2019 | Liu | G06V 10/17 |
| 2019/0104942 A1* | 4/2019 | Peru | A61B 5/0075 |
| 2020/0011735 A1 | 1/2020 | Laird et al. | |
| 2020/0411155 A1 | 12/2020 | O'Brien et al. | |
| 2022/0404361 A1* | 12/2022 | Sabry | G01N 33/56983 |

FOREIGN PATENT DOCUMENTS

| | | |
|---|---|---|
| TW | 201726059 | 8/2017 |
| TW | M572562 | 1/2019 |
| TW | M584970 | 10/2019 |
| TW | 202127311 | 7/2021 |

OTHER PUBLICATIONS

Texas Instruments Incorporated, "Signal Chain Performance Optimizations in the TI DLP®—Technology-Based Spectrometer", Sep. 2016, pp. 1-17. Available at: https://www.ti.com/lit/an/dlpa072/dlpa072.pdf.

* cited by examiner

DRUG SCANNING AND IDENTIFICATION SYSTEM AND USE METHOD THEREOF

CROSS-REFERENCE TO RELATED APPLICATION

This application claims the priority benefit of China application serial no. 202111206074.7, filed on Oct. 15, 2021. The entirety of the above-mentioned patent application is hereby incorporated by reference herein and made a part of this specification.

BACKGROUND

Technical Field

The disclosure relates to a spectral scanning system and a use method thereof, and more particularly to a drug scanning and identification system and a use method thereof.

Description of Related Art

Visual inspection is currently the most common method of drug identification. Visual inspection normally uses a visible light camera device to capture images of drugs for image analysis to obtain drug information. Although visual inspection can perform drug identification quickly, non-destructively, and pollution-free, many drugs do not have obvious marks in appearance, and their colors and shapes are very similar. For example, the common white round tablets can easily lead to misjudgment of images. In addition, if the inferior and counterfeit drugs have the same appearance but do not contain active pharmaceutical ingredients (API), then the visual inspection method can only be applied to inspect the appearance of the drug, and it is impossible to know the ingredients of the drug content.

The information disclosed in this Background section is only for enhancement of understanding of the background of the described technology and therefore it may contain information that does not form the prior art that is already known to a person of ordinary skill in the art. Further, the information disclosed in the Background section does not mean that one or more problems to be resolved by one or more embodiments of the disclosure was acknowledged by a person of ordinary skill in the art.

SUMMARY

The disclosure provides a drug scanning and identification system and a use method thereof, which can accurately identify the authenticity of drugs.

An embodiment of the disclosure provides a drug scanning and identification system, including a spectrometer, a drug holder, a mobile device and a drug identification model. The spectrometer includes a light source, a diffraction grating, a light-absorption element, a wavelength selector, and a single-point photodetector. The drug holder is disposed on the spectrometer and is adapted to position a drug under test. The drug holder includes a transparent area and a light-absorption area. The drug under test is disposed on the transparent area. The light-absorption area surrounds the transparent area. The mobile device is electrically connected to the spectrometer. The mobile device is adapted to send a control command to trigger the spectrometer scanning the drug under test so as to obtain spectrum data of the drug under test. The spectrometer is adapted to transmit the spectrum data of the drug under test to the drug identification model. The drug identification model is adapted to identify the spectrum data of the drug under test such that the drug identification model generates an identification result. The identification result is displayed by the mobile device.

In an embodiment of the disclosure, the drug identification model is implemented to the mobile device.

In an embodiment of the disclosure, the mobile device includes a controller and a storage device. The storage device has an application program (App), and the controller can execute the App, so that the mobile device can display the identification result, and the storage device has the drug identification model.

In an embodiment of the disclosure, a cloud server is further included. The cloud server is electrically connected to the mobile device, and the mobile device is adapted to transmit the spectrum data of the drug under test to the cloud server to identify the spectrum data of the drug under test, and the drug identification model is implemented to the cloud server.

In an embodiment of the disclosure, the cloud server includes a controller and a storage device, and the storage device has the drug identification model.

In an embodiment of the disclosure, in the process of scanning the drug under test by the spectrometer, the light source first emits incident light, and the incident light is irradiated on the drug under test, so that the drug under test receives the incident light and generates diffuse reflection light. The diffuse reflection light is incident onto the diffraction grating, and the diffraction grating divides the diffuse reflection light into a plurality of sub-diffuse reflection lights of different wavelengths. The plurality of sub-diffuse reflection lights are incident onto the wavelength selector. At the first time sequence, the wavelength selector makes one of the multiple sub-diffuse reflection lights incident onto the single-point photodetector, and then the sub-diffuse reflection light is received. At the second time sequence, the wavelength selector makes another one of the multiple sub-diffuse reflection lights incident onto the light-absorption element, and then the sub-diffuse reflection light is absorbed.

In an embodiment of the disclosure, an included angle between an incident direction of the incident light on the drug under test and the normal vector of the drug holder is within a range of 40 degrees to 50 degrees.

In an embodiment of the disclosure, the wavelength selector includes a plurality of pixels, and the plurality of sub-diffuse reflection lights are respectively incident onto the positions of different pixels of the wavelength selector.

In an embodiment of the disclosure, the spectrometer further includes a light collecting lens group, an entrance slit module, a collimating lens group, a band-pass filter, a focusing lens group, and a condenser lens group. The light source emits an incident light first, and the incident light is irradiated on the drug under test, so that the drug under test receives the incident light and generates the diffuse reflection light. The diffuse reflection light passes through the light collecting lens group, the entrance slit module, the collimating lens group, and the band-pass filter in sequence, and then is incident onto the diffraction grating. The diffraction grating divides the diffuse reflection light into multiple sub-diffuse reflection lights of different wavelengths, and the multiple sub-diffuse reflection lights pass through the focusing lens group and then are incident onto the wavelength selector. Then the plurality of sub-diffuse reflection lights are incident onto and penetrate the condenser lens group according to time sequence and then received by the single-point photodetector.

In an embodiment of the disclosure, the spectrometer further includes a positioning member, which is provided on the housing of the spectrometer and adapted to position the transparent area of the drug holder on the transmission path of incident light.

An embodiment of the disclosure provides a use method of a drug scanning and identification system, which includes the following steps. The first drug under test is placed on the drug holder on the first spectrometer. The mobile device is adapted to issue a control command to trigger the first spectrometer scanning the first drug under test, so as to obtain the first spectrum data of the first drug under test. The first spectrum data of the first drug under test is transmitted to the mobile device. The first spectrum data of the first drug under test is transmitted to the drug identification model. The drug identification model is adapted to identify the first spectrum data of the first drug under test to generate an identification result, and the identification result is displayed.

In an embodiment of the disclosure, the drug identification model is implemented to a mobile device or a cloud server.

In an embodiment of the disclosure, the drug identification model includes a first level of identification model and a second level of identification model. The first level of identification model includes multiple groups of drugs and the type of drug corresponding to each group in the multiple groups of drugs, active pharmaceutical ingredients (API) and a dose ratio between API and excipients. The second level of the identification model includes the dose ratio between multiple drugs and their corresponding API and excipients in each group of drug categories.

In an embodiment of the disclosure, the method further includes using multiple spectrometers to establish a database. The multiple spectrometers include a first spectrometer and at least one second spectrometer. The first drug under test is placed on the drug holder of the first spectrometer. The first spectrometer scans the first drug under test to obtain the first spectrum data. At least one second drug under test is placed on the drug holder of the at least one second spectrometer. The at least one second spectrometer respectively scans at least one second drug under test to obtain at least one second spectrum data of the at least one second drug under test. The first spectrum data and the at least one second spectrum data are calculated to establish a database having the first spectrum data of the first drug under test and the second spectrum data of the at least one second drug under test.

In an embodiment of the disclosure, the first drug under test and the second drug under test are the same drug. The first spectrum data and the second spectrum data are interpolated. The first spectrum data and the second spectrum data are smoothed and equidistantly interpolated, so that the spectra in the first spectrum data and the second spectrum data form consistent wavelength position information.

In an embodiment of the disclosure, the step of using the drug identification model to identify the first spectrum data of the first drug under test to obtain the identification result of the first drug under test and displaying the identification result further includes: selecting a classification mode or a qualification mode through a menu interface of the mobile device.

In an embodiment of the disclosure, when the classification mode is selected, the spectrum data of the drug most similar to the first spectrum data of the first drug under test is searched in the drug identification model, and there is a minimum error value between the spectrum data of the most similar drug and the first spectrum data of the first drug under test, so as to obtain the identification result of the first drug under test. The identification result is, for example, the name of the drug, the main ingredient, the content of the main ingredient, the drug manufacturer and the spectrum data.

In an embodiment of the disclosure, when the qualification mode is selected, the name of the predetermined drug is input to find the spectrum data of the predetermined drug. Then the drug identification model is adapted to compare the first spectrum data of the first drug under test and the spectrum data of the predetermined drug and find out whether they are consistent. If the comparison result is positive, the mobile device displays "matched", otherwise, if they are not consistent, the mobile device displays "not matched".

Based on the foregoing, in an embodiment of the disclosure, since the drug scanning and identification system and a use method thereof adopt a near-infrared spectroscopy scanning technology to inspect the contents of the drug under test, it is possible to solve the blind spot problem of visual inspection of drugs.

Other objectives, features and advantages of the present disclosure will be further understood from the further technological features disclosed by the embodiments of the present disclosure wherein there are shown and described preferred embodiments of this disclosure, simply by way of illustration of modes best suited to carry out the disclosure.

BRIEF DESCRIPTION OF THE DRAWINGS

The accompanying drawings are included to provide a further understanding of the disclosure, and are incorporated in and constitute a part of this specification. The drawings illustrate of the disclosure and, together with the description, serve to explain the principles of the disclosure.

DESCRIPTION OF THE EMBODIMENTS

In the following detailed description of the preferred embodiments, reference is made to the accompanying drawings which form a part hereof, and in which are shown by way of illustration specific embodiments in which disclosure may be practiced. In this regard, directional terminology, such as "top," "bottom," "front," "back," etc., is used with reference to the orientation of the Figure(s) being described. The components of the present disclosure can be positioned in a number of different orientations. As such, the directional terminology is used for purposes of illustration and is in no way limiting. On the other hand, the drawings are only schematic and the sizes of components may be exaggerated for clarity. It is to be understood that other embodiments may be utilized and structural changes may be made without departing from the scope of the present disclosure. Also, it is to be understood that the phraseology and terminology used herein are for the purpose of descript ion and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. Similarly, the terms "facing," "faces" and variations thereof herein are used broadly and encompass direct and indirect facing, and "adjacent to" and variations thereof herein are used broadly and encompass directly and indirectly "adjacent to". Therefore, the description of "A" component facing "B" component herein may contain the situations that "A" component directly faces "B" component or one or more additional components are between "A" component and "B" component. Also, the description of "A" component "adjacent to" "B" component herein may contain the situation that "A" component is directly "adjacent to" "B" component or one or more additional components are between "A" component and "B" component. Accordingly, the drawings and descriptions will be regarded as illustrative in nature and not as restrictive.

Figure 1:
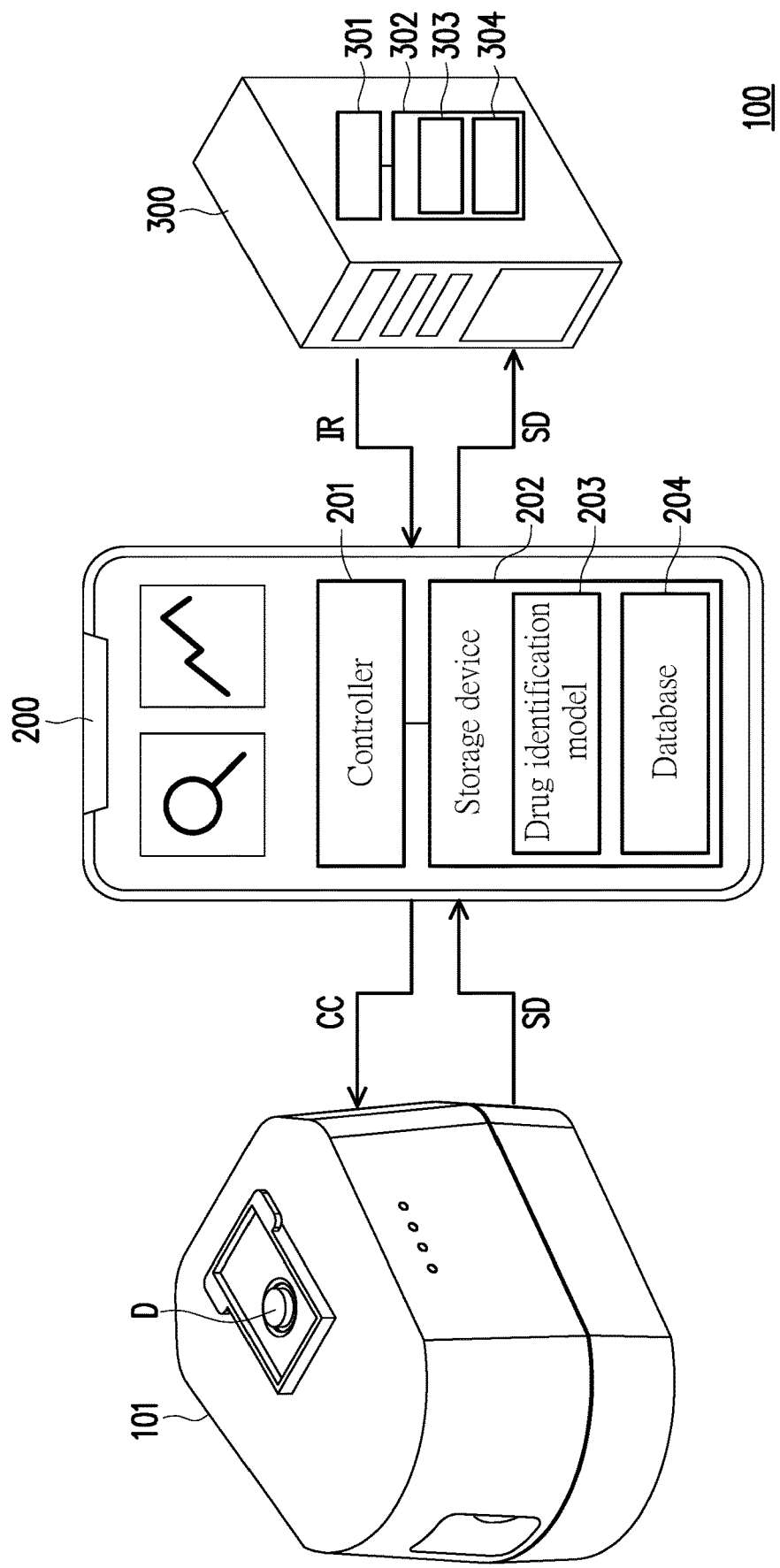
FIG. 1 is a schematic diagram of a drug scanning and identification system according to an embodiment of the disclosure.
Figure 2:
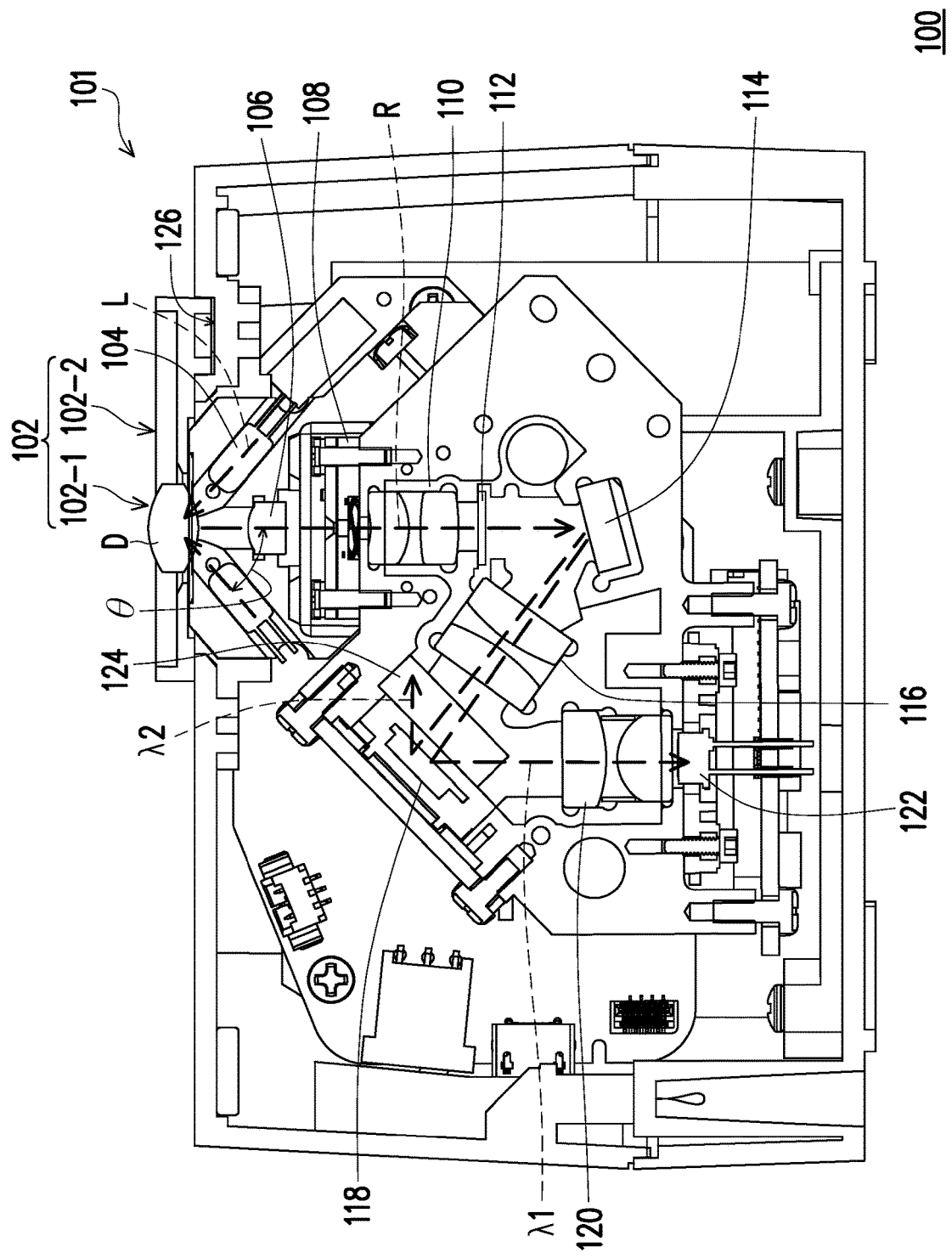
FIG. 2 is a schematic diagram of the inside of a spectrometer of a drug scanning and identification system according to an embodiment of the disclosure.

FIG. 1 is a schematic diagram of a drug scanning and identification system according to an embodiment of the disclosure. FIG. 2 is a schematic diagram of the inside of a spectrometer of the drug scanning and identification system according to an embodiment of the disclosure. Please refer to FIG. 1 and FIG. 2 first. An embodiment of the disclosure provides a drug scanning and identification system 100. The drug scanning and identification system 100 includes a spectrometer 101, a mobile device 200 and a cloud server 300. The mobile device 200 is electrically connected to the spectrometer 101 and the cloud server 300. The mobile device 200 is adapted to issue a control command CC to trigger the spectrometer 101 scanning the drug under test D to obtain spectrum data SD of the drug under test D. The spectrometer 101 is adapted to transmit the spectrum data SD of the drug under test D to the mobile device 200. The mobile device 200 transmits the spectrum data SD of the drug under test D to the cloud server 300. The cloud server 300 is adapted to identify the spectrum data SD of the drug under test D. The cloud server 300 has a drug identification model for identifying the spectrum data SD of the drug under test D to generate an identification result IR. The cloud server 300 transmits the identification result IR to the mobile device 200, and the mobile device 200 displays the identification result IR to the user. The mobile device 200 has a display screen for displaying the identification result IR.

In this embodiment, the mobile device 200 can be a smart phone, a laptop or a tablet computer, but the disclosure is not limited thereto. The mobile device 200 includes a controller 201 and a storage device 202. The storage device 202 has an App, the App has a menu interface, and the controller can execute the App, so that the mobile device 200 allows the user to choose the function they want to use, and the mobile device 200 can display the identification result IR to the user. The cloud server 300 includes a controller 301 and a storage device 302. The storage device 302 of the cloud server 300 has a drug identification model 303. The drug identification model 303 is a software program, and the controller 301 can execute the drug identification model 303 to identify the spectrum data SD of the drug under test D. In addition, the storage device 302 may further include a database 304 for storing spectrum data of various types of drugs and for generating the drug identification model 303. In other embodiments, the cloud server 300 may transmit the generated drug identification model 303 to the mobile device 200. The drug identification model 303 is stored in the storage device 202 of the mobile device 200, and the controller 201 of the mobile device 200 can execute the drug identification model 203 to identify the spectrum data SD of the drug under test D. The drug scanning and identification system of the disclosure can update the drug identification model through the cloud server 300.

As shown in FIG. 2, the drug holder 102 is disposed on the spectrometer 101, and the drug holder 102 and the spectrometer 101 are separable. The spectrometer 101 includes a light source 104, a diffraction grating 114, a light-absorption element 124, a wavelength selector 118, and a single-point photodetector 122. Specifically, the drug holder 102 is adapted for positioning the drug under test D. The drug holder 102 can fix the position of the drug under test D according to the contour (for example, an ellipse or a circle, etc.) of the drug under test D. The drug holder 102 includes a transparent area 102-1 and a light-absorption area 102-2. The drug under test D is placed in the transparent area 102-1, and the light-absorption area 102-2 surrounds the transparent area 102-1. The transparent area 102-1 is an opening, and the light-absorption area 102-2 is made of, for example, a material with carbon black and an absorption rate of near-infrared light greater than and equal to 98%.

In this embodiment, the light source 104 is, for example, a vacuum tungsten lamp, a laser light source, a light emitting diode (LED) or other suitable light sources. When the spectrometer 101 scans the drug under test D, the light source 104 emits incident light L first. The main wavelength of the incident light L preferably falls within a band of near-infrared light, and the band ranges from, for example, 900 nm to 2500 nm. The drug under test D is placed in the transparent area 102-1, and the incident light L passes through the transparent area 102-1 to irradiate the drug under test D, so that the drug under test D receives the incident light L and generates diffuse reflection light R. The diffuse reflection light R is incident onto the diffraction grating 114, and the diffraction grating 114 may be a reflective diffraction grating. The diffraction grating 114 divides the diffuse reflection light R into a plurality of sub-diffuse reflection lights λ1 and λ2 of different wavelengths. The sub-diffuse reflection lights λ1 and λ2 are incident onto the wavelength selector 118. For example, at the first time sequence, the wavelength selector 118 makes the sub-diffuse reflection light λ1 incident onto the single-point photodetector 122 and then be received, and makes the sub-diffuse reflection light λ2 incident onto the light-absorption element 124 and then be absorbed. At the second time sequence, the wavelength selector 118 makes the sub-diffuse reflection light λ2 incident onto the single-point photodetector 122 and then be received, and makes the sub-diffuse reflection light λ1 incident onto the light-absorption element 124 and then be absorbed. The light-absorption element 124 is, for example, a near-infrared absorber (NIR absorber)

which prevents light from being reflected inside the spectrometer 101 and causing stray light, so that the signal to noise ratio (SNR) of the spectrometer 101 can be significantly improved, and the accuracy of the spectrum data SD can be ensured.

In this embodiment, the spectrometer 101 further includes a light collecting lens group 106, an entrance slit module 108, a collimating lens group 110, a band-pass filter 112, a focusing lens group 116, and a condenser lens group 120. The entrance slit module 108 can be formed by electroforming or laser processing. The band-pass filter 112 is fabricated by coating a film on a transparent substrate, and the band-pass filter 112 can exclude light with a wavelength below 900 nanometers (nm). Specifically, the diffuse reflection light R passes through the light collecting lens group 106, the entrance slit module 108, the collimating lens group 110, and the band-pass filter 112 in sequence, and then incidents on the diffraction grating 114. The sub-diffuse reflection lights $\lambda 1$ and $\lambda 2$ pass through the focusing lens group 116 and then incident onto the wavelength selector 118. The sub-diffuse reflection lights $\lambda 1$ and $\lambda 2$ are incident onto and penetrate the condenser lens group 120 according to the time sequence, and then received by the single-point photodetector 122.

In addition, in an embodiment, the light collecting lens group 116, the collimating lens group 110, the focusing lens group 116 and the condenser lens group 120 are preferably made of optical glass, and their surfaces may be coated with an anti-reflective film with near-infrared wavelengths.

In this embodiment, the included angle $\theta$ between the incident direction of the incident light L on the drug under test D and the normal vector of the drug holder 102 preferably falls within the range of 40 degrees to 50 degrees, as shown in FIG. 2.

In this embodiment, the drug scanning and identification system 100 further includes a positioning member 126. The positioning member 126 is arranged on the housing of the spectrometer 101 and is adapted to position the transparent area 102-1 of the drug holder 102 on the transmission path of the incident light L. In another embodiment, the positioning member 126 can be integrally formed with the housing of the spectrometer 101. In this embodiment, the positioning member 126 is a groove for fixing the drug holder 102. In other embodiments, the positioning member 126 may be a plurality of protrusions, and the plurality of protrusions surround an area for fixing the drug holder 102. The form of the positioning member 126 is not limited thereto.

Figure 3:
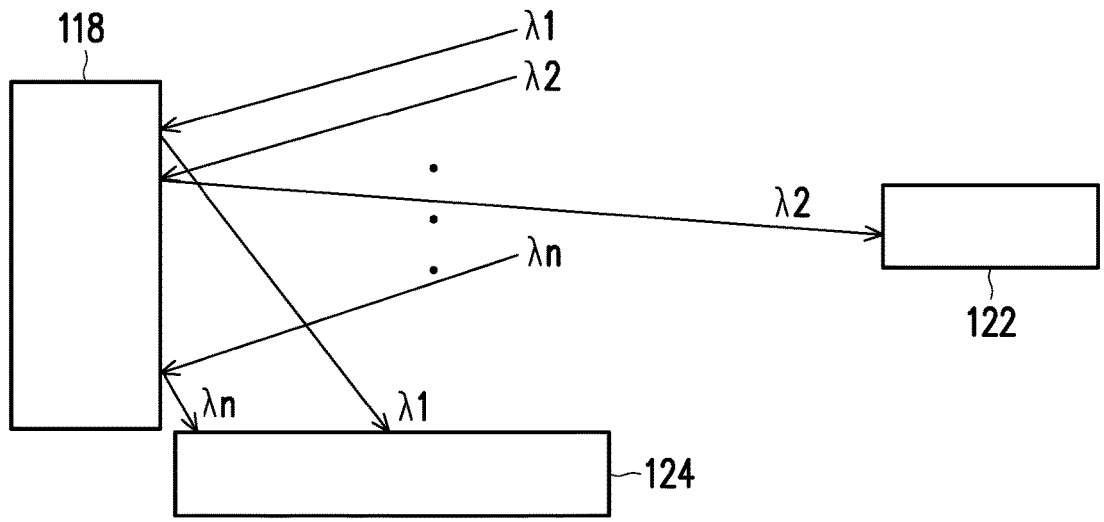
FIG. 3 is a schematic diagram showing the transmission of sub-diffuse reflection light.

FIG. 3 is a schematic diagram showing the transmission of sub-diffuse reflection light. Please refer to FIG. 2 and FIG. 3, in this embodiment, the wavelength selector 118 and the light-absorption element 124 are located on the transmission path of the sub-diffuse reflection lights $\lambda 1$ and $\lambda 2$. At the second time sequence, the light-absorption element 124 is located on the transmission path where the sub-diffuse reflection lights $\lambda 1$ and $\lambda 3$ . . . $\lambda n$ are reflected by the wavelength selector 118, except for the sub-diffuse reflection light $\lambda 2$. At the second time sequence, the sub-diffuse reflection light $\lambda 2$ is reflected by the wavelength selector 118 to the single-point photodetector 122. In addition, at the first time sequence, the light-absorption element 124 is located on the transmission path where the sub-diffuse reflection lights $\lambda 2$ and $\lambda 3$ . . . $\lambda n$ are reflected by the wavelength selector 118, except for the sub-diffuse reflection light $\lambda 1$. At the first time sequence, the sub-diffuse reflection light $\lambda 1$ is reflected by the wavelength selector 118 to the single-point photodetector 122. The other sub-diffuse reflection lights are reflected by the wavelength selector 118 to the single-point photodetector 122 according to the time sequence.

In addition, in this embodiment, the wavelength selector 118 may be a digital micro-mirror device (DMD) or a liquid-crystal-on-silicon panel (LCOS Panel). The wavelength selector 118 may include a plurality of pixels 118-1 and 118-2, and the sub-diffuse reflection lights $\lambda 1$ and $\lambda 2$ are incident onto different pixels 118-1 and 118-2 of the wavelength selector 118, respectively.

Figure 4:
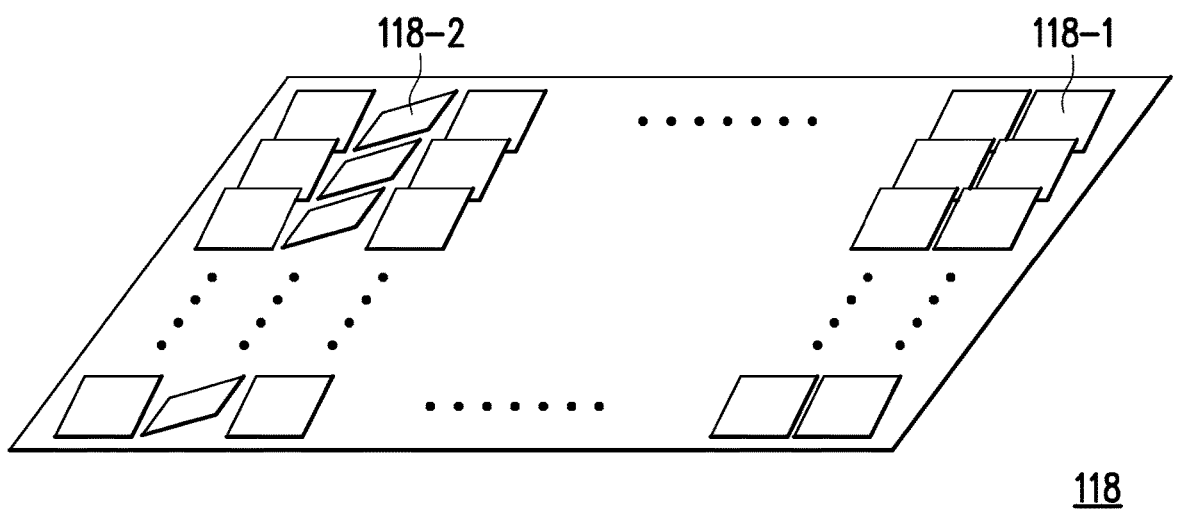
FIG. 4 is a schematic diagram of a wavelength selector controlling its pixel deflection at different time sequences.

FIG. 4 is a schematic diagram of a wavelength selector controlling its pixel deflection at different time sequences. FIG. 4 is illustrated with a DMD as an example, and each of the pixels 118-1 and 118-2 is arranged in an array. These pixels 118-1 and 118-2 can be micro mirrors, and their deflection direction can be controlled by means of software or hardware. For example, when each pixel 118-2 is controlled in the ON state, as shown in FIG. 4, at the first time sequence, the sub-diffuse reflection light $\lambda 1$ incident onto the pixel 118-2 will be reflected to the single-point photodetector 122. On the contrary, for the remaining pixels 118-1 controlled in the OFF state, the incident sub-diffuse reflection light $\lambda 2$ will be reflected to the light-absorption element 124.

In this embodiment, the wavelength selector 118 is controlled to respectively output multiple sub-diffuse reflection lights of different wavelength ranges at multiple different time sequences, and then the single-point photodetector 122 is adapted to integrate the received signals at different time sequences, so as to obtain the spectrum data SD of the drug under test D. In other words, the pixels 118-1 and 118-2 in the wavelength selector 118 are respectively controlled to be in the ON state at different time sequences, so that the sub-diffuse reflection lights $\lambda 1$ and $\lambda 2$ are reflected to the single-point photodetector 122 at different time sequences according to their wavelength ranges.

Based on the above, in an embodiment of the disclosure, since the spectrometer 101 of the drug scanning and identification system 100 uses the near-infrared spectroscopy scanning technology to obtain the API, excipients and other contents contained in the drug under test D, it is possible to solve the blind spot problem of visual inspection of drugs. Moreover, the spectrometer 101 of the drug scanning and identification system 100 adopts a single-point photodetector 122. Compared with the use of an array-type photodetector, the spectrometer 101 of the drug scanning and identification system 100 of the embodiment of the disclosure costs less.

Figure 5:
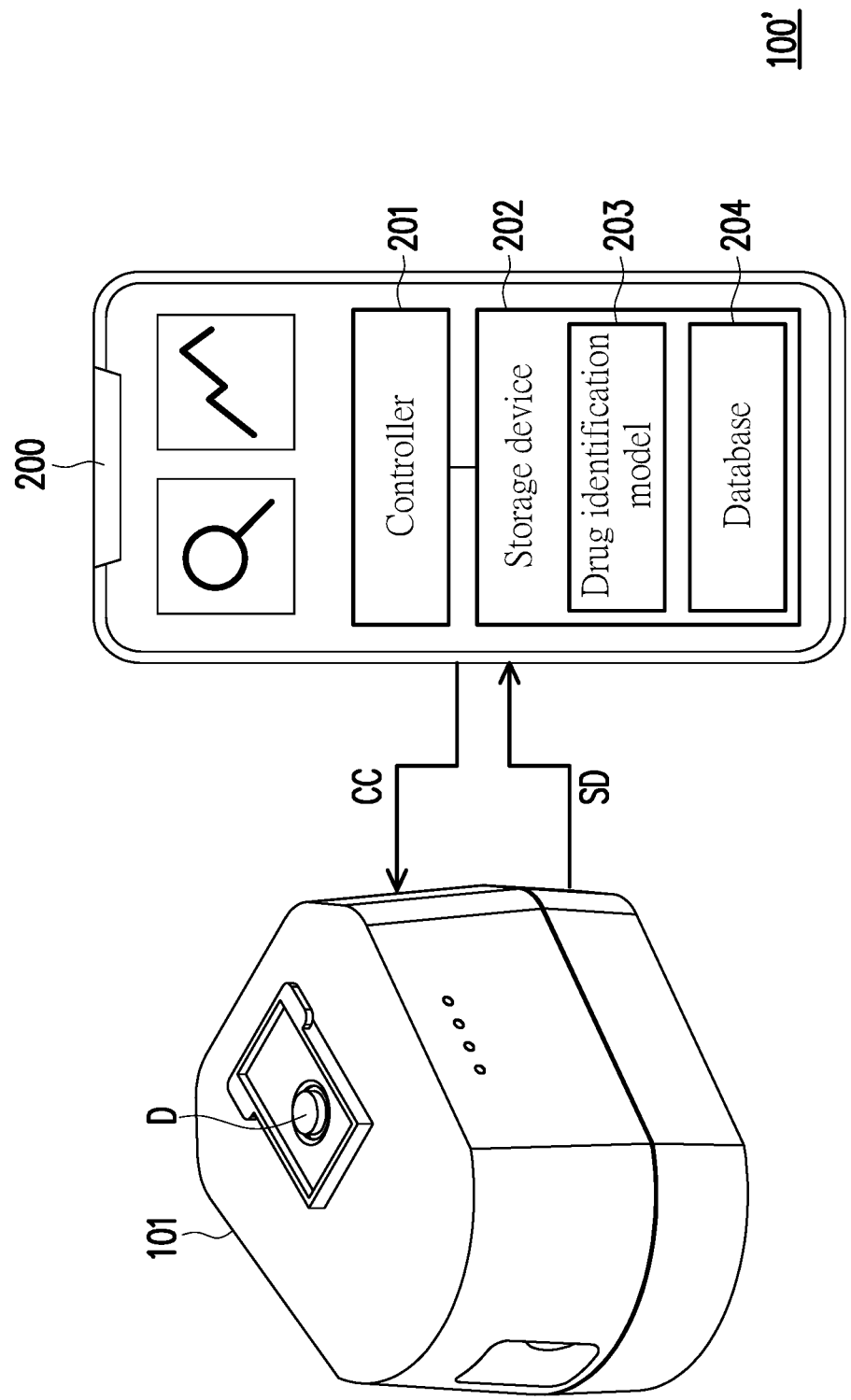
FIG. 5 is a schematic diagram of a drug scanning and identification system according to another embodiment of the disclosure.

FIG. 5 is a schematic diagram of a drug scanning and identification system according to another embodiment of the disclosure. An embodiment of the disclosure provides a drug scanning and identification system 100'. The drug scanning and identification system 100' includes a spectrometer 101 and a mobile device 200. The mobile device 200 is electrically connected to the spectrometer 101. The mobile device 200 is adapted to issue a control command CC to trigger the spectrometer 101 scanning the drug under test D to obtain the spectrum data SD of the drug under test D. The spectrometer 101 is adapted to transmit the spectrum data SD of the drug under test D to the mobile device 200. The mobile device 200 is adapted to identify the spectrum data SD of the drug under test D, and the mobile device 200 has a drug identification model for identifying the spectrum data SD of the drug under test D to generate an identification result IR. The mobile device 200 generates an identification result IR and displays it to the user.

In this embodiment, the mobile device 200 can be a smart phone, a laptop or a tablet computer, but the disclosure is not limited thereto. The mobile device 200 includes a controller 201 and a storage device 202. The storage device 202 has an App, and the controller can execute the App, so that the mobile device 200 can display the identification result IR for the user to watch. The storage device 202 of the mobile device 200 has a drug identification model 203. The drug identification model 203 is a software program and an artificial intelligence model. The controller 201 can execute the drug identification model 203 to identify the spectrum data SD of the drug under test D. In addition, the storage device 202 may further include a database 204 for storing spectrum data of various types of drugs, and for generating the drug identification model 203. In other embodiments, the mobile device 200 can store the generated drug identification model 203 in the storage device 202 of the mobile device 200, and the mobile device 200 can update the drug identification model.

Figure 6:
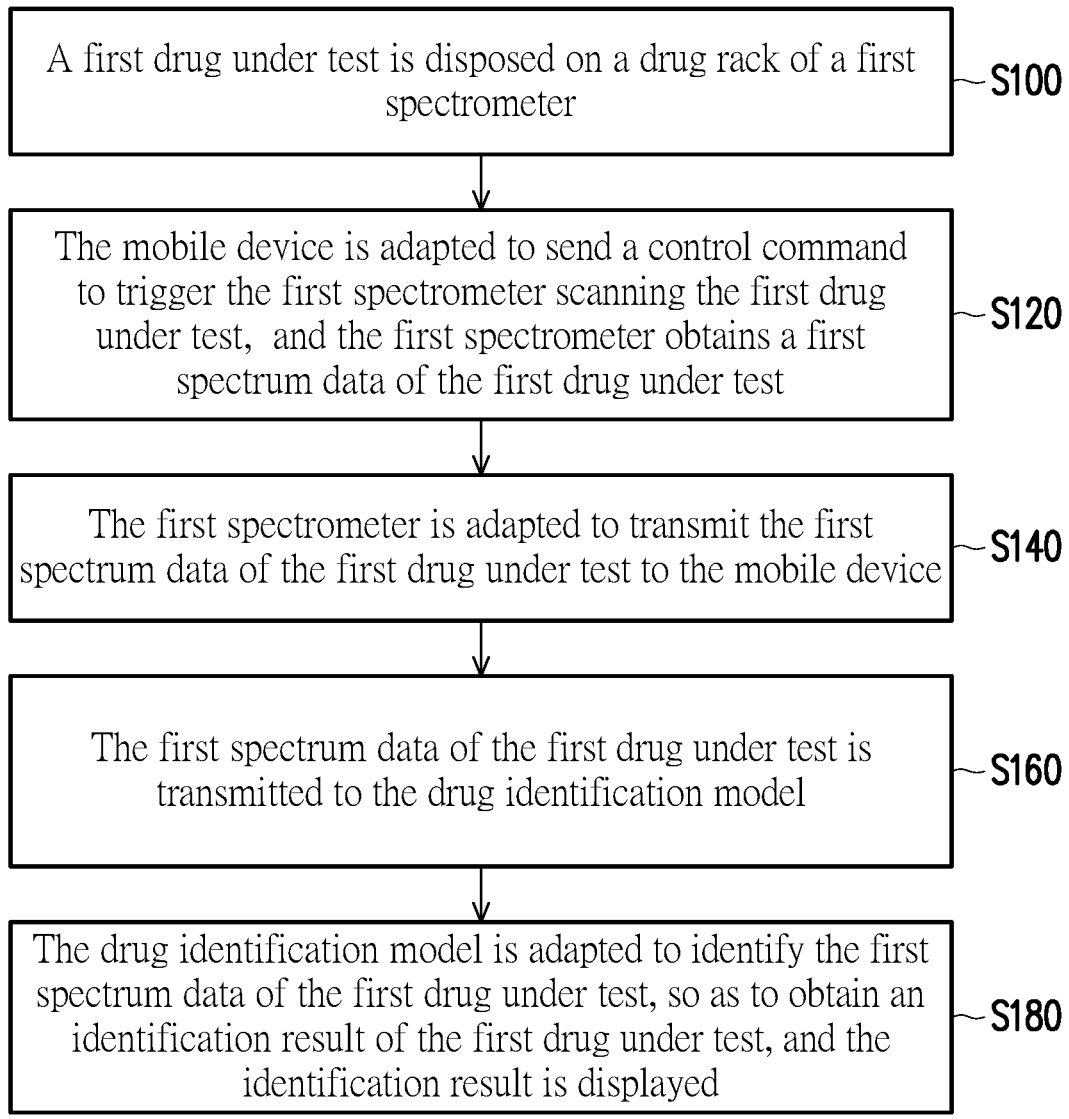
FIG. 6 is a flowchart of a use method of a drug scanning and identification system according to an embodiment of the disclosure.

FIG. 6 is a flowchart of a use method of a drug scanning and identification system according to an embodiment of the disclosure. Please refer to FIG. 6, an embodiment of the disclosure provides a use method of a drug scanning and identification system (such as FIG. 1 or FIG. 5), which includes the following steps. The first drug under test D is placed on the drug holder 102 on the first spectrometer 101, which is step S100. The mobile device 200 is adapted to issue a control command CC to trigger the first spectrometer 101 scanning the first drug under test D, so that the first spectrometer 101 obtains the first spectrum data SD of the first drug under test D, which is step S120. The first spectrum data SD of the first drug under test D is transmitted to the mobile device 200 by the first spectrometer 101, which is step S140. The first spectrum data SD of the first drug under test D is transmitted to the drug identification model, which is, for example, the drug identification model 303 implemented to the cloud server 300 or the drug identification model 202 implemented to the mobile device 200, which is step S160. The drug identification model is adapted to identify the first spectrum data SD of the first drug under test D to obtain the identification result IR of the first drug under test D, and the identification result IR is displayed, which is step S180.

It should be noted that step S160 further includes a step of establishing a database and establishing a drug identification model. The step is described as follows.

In this embodiment, the above-mentioned mobile device 200 or cloud server 300 can establish databases 204 and 304 with spectrum data of drug under test. The databases are established by accumulating spectrum data obtained by spectrum-scanning brand-name drugs by a spectrometer. In addition to having spectrum data of drugs, the databases 204 and 304 also contain drug classification, ATC (Anatomical Therapeutic Chemical Classification) code, drug name, main ingredient, content of main ingredient, and hyperlinks of drug manufacturers and food and drug management authorities in various countries. The aforementioned identification result IR is, for example, at least one of a certain drug's spectrum data (graphic), ATC code, drug name, main ingredient and content thereof, and hyperlinks of drug manufacturers and food and drug management authorities in various countries. The identification result IR can be displayed in the mobile device 200.

Figure 7:
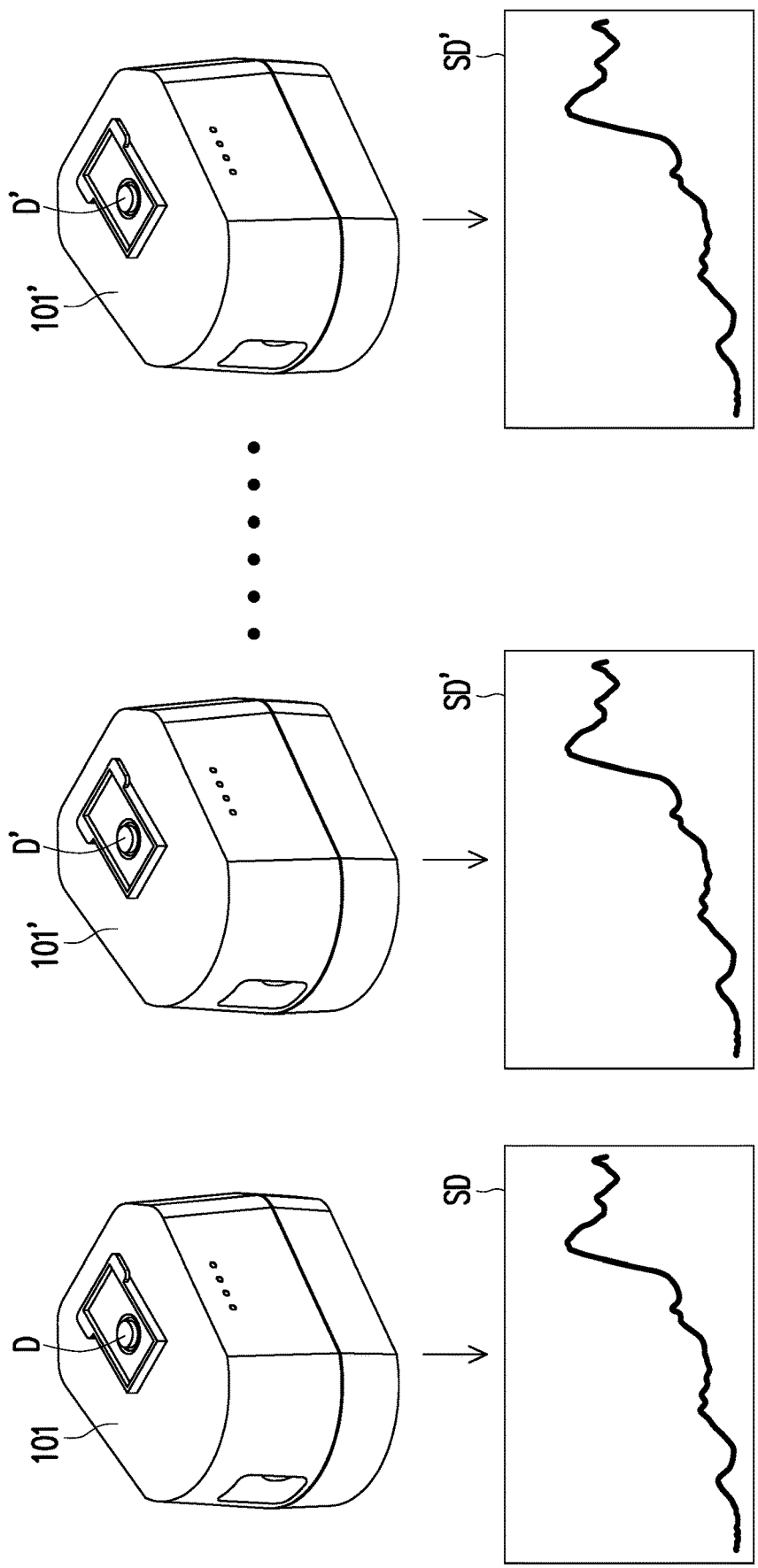
FIG. 7 is a schematic diagram of obtaining spectrum data of a drug under test by using multiple spectrometers.

FIG. 7 is a schematic diagram of obtaining spectrum data of a drug under test by using multiple spectrometers. Please refer to FIG. 1 and FIG. 7. In this embodiment, multiple spectrometers are adapted to establish databases 204 and 304 having spectrum data of drug under test. As shown in FIG. 7, the first drug under test D is placed on the drug holder on the first spectrometer 101. The first spectrometer 101 scans the first drug under test D to obtain the first spectrum data SD. At least one second drug under test D' is placed on the drug holder on the at least one second spectrometer 101'. At least one second spectrometer 101' respectively scans at least one second drug under test D' to obtain at least one second spectrum data SD' of the at least one second drug under test D'. The second spectrum data SD' of the second drug under test D' is transmitted to the mobile device 200 or the cloud server 300. The controllers 201 and 301 of the mobile device 200 or the cloud server 300 calculate the first spectrum data SD and the second spectrum data SD' to establish databases 204 and 304 having the first spectrum data SD of the first drug under test D and the second spectrum data SD' of the at least one second drug under test D'. Specifically, the elements in the second spectrometer 101' and the optical path and method for scanning the second drug under test D' are the same as those of the first spectrometer 101, and no further description is incorporated herein.

It should be mentioned that due to differences in hardware or software between spectrometers, the spectrum data (such as wavelength position) obtained by inspecting the same drug will not be the same, so the following methods are adopted to solve the above problems. As shown in FIG. 7, when the first drug under test D and the second drug under test D' are the same drug, that is to say, when the spectrometers 101 and 101' scan the same drug under test D and D', the spectrum data SD and SD' can be smoothed and equidistantly interpolated through interpolation (such as cubic spline resampling). In this way, the spectra in each spectrum data SD and SD' will have consistent wavelength position information to resolve the differences between the spectrometers.

In this embodiment, after the above-mentioned database is established, a drug identification model can be generated based on the above-mentioned database. The method of establishing the drug identification model is described as follows.

In this embodiment, before describing how to establish the drug identification model, the constitution of the drug identification model is explained. The drug identification model includes a first level of identification model and a second level of identification model. Specifically, the first level of identification model includes multiple groups of drugs and the type of drug corresponding to each group in the multiple groups of drugs, API and a dose ratio between API and excipients. The second level of the identification model includes the dose ratio between multiple drugs and their corresponding API and excipients in each group of drug categories. To be more specific, the first level of identification model is a structured drug classification and coding system commonly used in the world, such as AHFS/DI (American Hospital Formulary Service/Drug information) and WHO/ATC (World Health Organization/Anatomical Therapeutic Chemical Classification) in the U.S. For example, the classification code of multi-group drugs including diabetes drug is A10, and the classification code of blood lipid regulator is C10. Therefore, the first level of identification model can identify drugs with different active pharmaceutical ingredients (API) to achieve over 99% drug identification ability. The second level of identification model is to identify drugs with the same API but with different dose ratios between API and excipients in each group of drug categories, and can also reach 99.5% or even more than 99.8% identification ability.

For example, the common API of blood lipid drugs include Atorvastatin, Fenofibrate, Gemfibrozil, Pitavastatin, Pravastatin, Simvastatin, etc. The drugs with Atorvastatin as API involve research drugs and a variety of generic drugs with different doses, such as 10 mg, 20 mg, or 40 mg. Because there are a variety of combinations of API and excipients, and in order to prevent the drug identification model from being interfered by excipients and overfitting, the first level of identification model does not take an excess of principal components. The second level of identification model limits/restricts the API, and therefore is capable of summarize new principal components based on the dose difference between the API and the excipients. As such, the accuracy of drug identification can be significantly improved.

In this embodiment, the establishment process of the drug identification model is described as follows. Both the first level of identification model and the second level of identification model of the drug identification model can be established based on the following process.

Taking blood lipid drugs as an example, a drug identification model is established for about 8000 spectrum data of 80 kinds of drugs. An equidistant interpolation operation is adopted for establishing the database. Specifically, equidistant interpolation includes linear interpolation and cubic spline interpolation. The interval of interpolation can be adjusted depending on the spectral resolution, for example, take 2 nm as the interval. The wavelength range can be selected to best identify the drug, such as 900 nm to 1650 nm. In addition, differentiation and smoothing are, for example, performed by using Savitzky-Golay smoothing & derivation method, and the parameters, such as differential order and window size, of the drug identification model can be adjusted and smoothed according to circumstances, for example, by using first order differential and including nine wavelength points in the window range. There are many options for category analysis algorithms. Linear discriminant analysis (LDA) or Mahalanobis distance may be adopted, and the results of principle component analysis (PCA) will also be adopted to specify the number of principle component (PC). The number of PC can be adjusted depending on the needs to ensure the robustness and correctness of the drug identification model. The LDA is adopted to establish the first level of the identification model. LDA and Mahalanobis distance are adopted for analysis to establish the second level of the identification model. The establishment of the drug identification model is completed through the establishment of the first level of identification model and the second level of identification model.

Figure 8A:
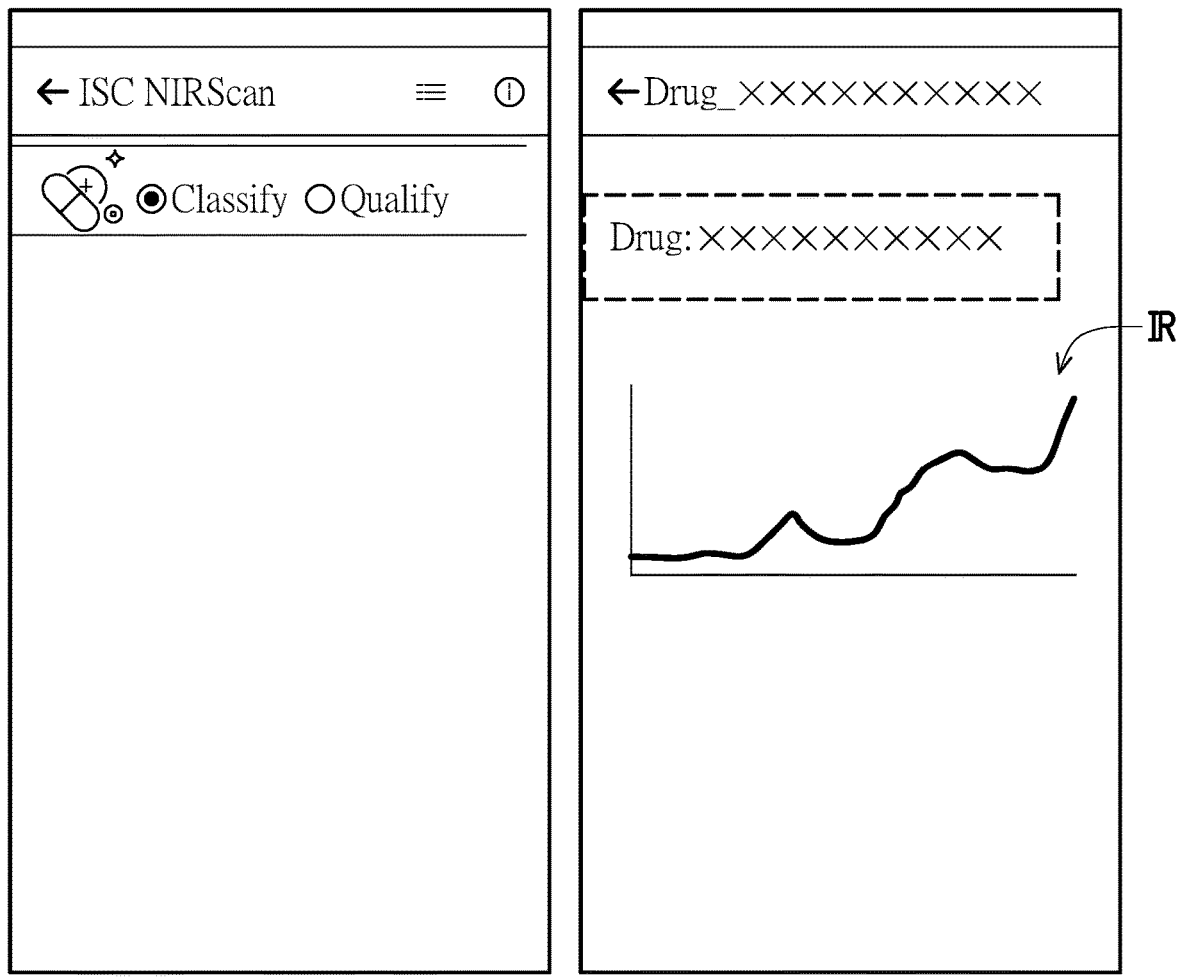
FIG. 8A is a schematic diagram of a display screen of a mobile device of the drug scanning and identification system of the disclosure.
Figure 8B:
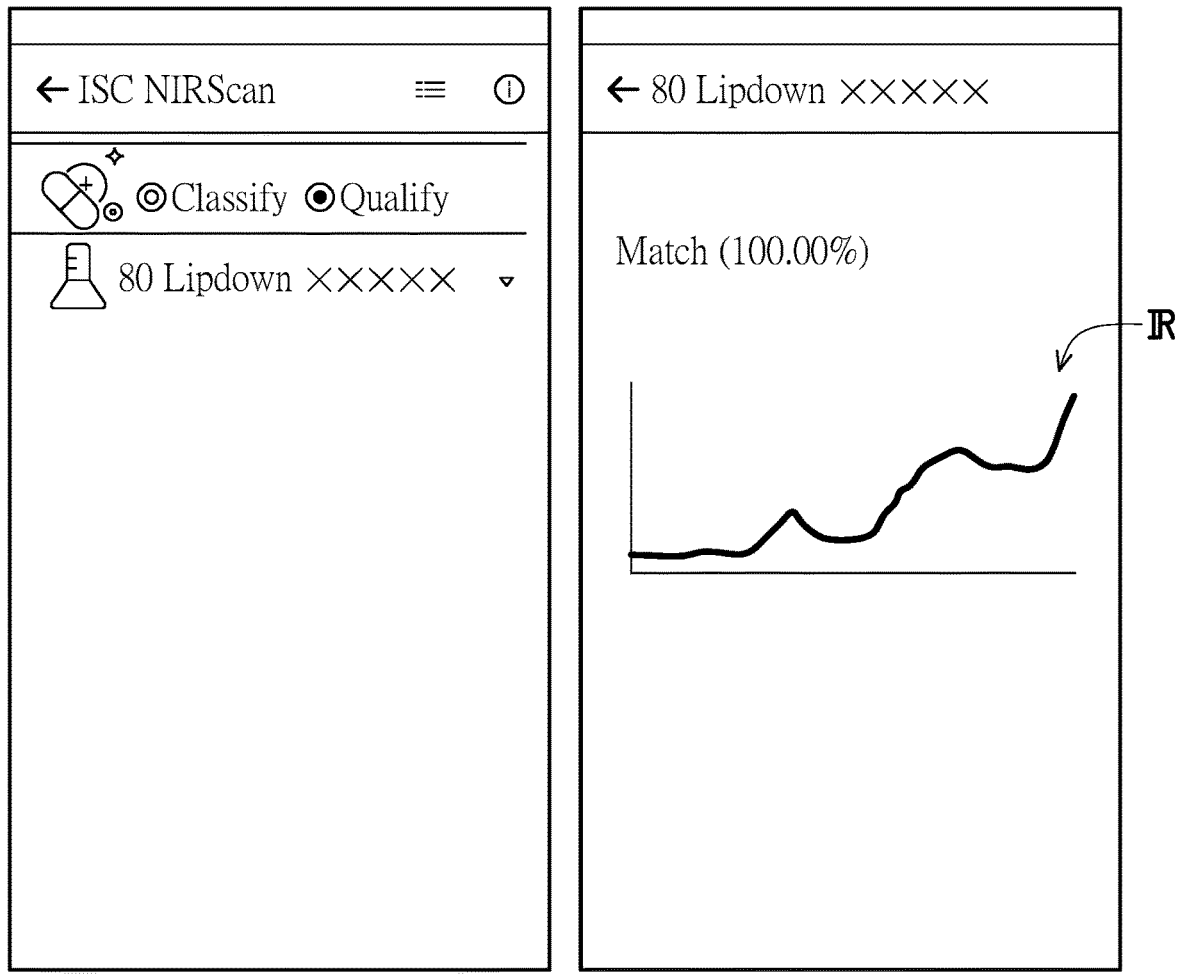
FIG. 8B is a schematic diagram of another display screen of the mobile device of the drug scanning and identification system of the disclosure.

FIG. 8A is a schematic diagram of a display screen of a mobile device of the drug scanning and identification system of the disclosure. FIG. 8B is a schematic diagram of another display screen of the mobile device of the drug scanning and identification system of the disclosure. In this embodiment, the step S180 of using the drug identification model to identify the first spectrum data SD of the first drug under test D to obtain the identification result of the first drug under test D further includes using a menu interface of the App of the mobile device 200 to select the classification mode or the qualification mode. Referring to FIG. 8A, when the first drug under test D is a drug that the user does not know, the user selects the classification mode to obtain the identification result IR (for example, drug name) of the first drug under test D, which includes the following steps. In the drug identification model, the spectrum data of the drug that is most similar to the first spectrum data SD of the first drug under test D is looked for. The spectrum data of the most similar drug refers to the spectrum data having the minimum error value relative to the first spectrum data SD of the first drug under test D in the database.

The identification result IR with the most similar drug is displayed on the mobile device 200 for the user to view. The identification result IR includes, for example, drug name, main ingredient, content of main ingredient, drug manufacturer and the spectrum data.

Referring to FIG. 8B, when the first drug under test D is a drug that the user knows, and the user wants to know the authenticity of the first drug under test D, the user selects the qualification mode to verify the identification result IR of the first drug under test D, which includes the following steps. The name of the predetermined drug is input. In the database, the spectrum data of the predetermined drug is searched. The drug identification model is adapted to compare whether the first spectrum data SD of the first drug under test D is consistent with the spectrum data of the predetermined drug in the database. If the result is positive, then the mobile device 200 displays "matched". On the contrary, if they are not consistent, then the mobile device 200 displays "not matched".

In addition, the menu interface of the App further includes a hyperlink path, which allows users to access websites of food and drug management authorities in various countries through this hyperlink path, so as to further compare whether the appearance and packaging of the first drug under test D are consistent with that of brand-name drug, so that the drug identification steps are complete.

The above process of identifying or establishing spectrum data of drug under test can adopt a mobile device or a cloud server. On the one hand, the drug scanning and identification system performs the spectrum scanning on the drug under test, and on the other hand, the obtained spectrum data of the drug under test can be input into the drug identification model for drug identification, and a predictive identification result can be obtained. The drug identification model can be downloaded from the cloud server by the mobile device through the user's operation, or directly installed in the mobile device.

Furthermore, the drug scanning and identification system can scan, identify or establish spectrum data of the drug under test through one or more controllers electrically connected to the spectrometer, mobile device or cloud server. For example, the spectrometer may include one or more controllers. These controllers are electrically connected to the light source, wavelength selector and single-point photodetector, and control the operation of various elements. The mobile device may include one or more controllers, and control the operation of the drug scanning and identification system through these controllers, and the drug identification model can identify the spectrum data of the drug under test.

In an embodiment, the controller includes, for example, a microcontroller unit (MCU), a central processing unit (CPU), a microprocessor, a digital signal processor (DSP), a programmable controller, a programmable logic device (PLD) or other similar devices or a combination of these devices, the disclosure provides no limitation thereto. In addition, in an embodiment, the functions of the controller can be implemented as a plurality of program codes. These codes are stored in a memory, and the controller will execute these codes. Alternatively, in an embodiment, the functions of the controller may be implemented as one or more circuits. The disclosure provides no limitation to the use of software or hardware to implement the functions of the controller. The storage device is, for example, a removable random access memory (RAM), a read-only memory (ROM), a flash memory or similar elements or a combination of the above elements, and the storage device is adapted to store spectrum data, drug identification models and Apps.

In summary, in an embodiment of the disclosure, since the drug scanning and identification system and a use method thereof adopt the near-infrared spectroscopy scanning technology to inspect the API, excipients, etc. contained in the drug under test, it is possible to solve the blind spot problem of visual inspection of drugs.

The foregoing description of the preferred embodiments of the disclosure has been presented for purposes of illustration and description. It is not intended to be exhaustive or to limit the exemplary disclosure to the precise form or to embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the disclosure and its best mode practical application, thereby enable persons skilled in the art to understand the disclosure for various embodiments and with various modifications as are suited to the particular use or implementation contemplated. It is intended that the scope of the disclosure be defined by the claims appended hereto and their equivalents in which all terms are meant in their broadest reasonable sense unless otherwise indicated. Therefore, the term "the disclosure", "the present disclosure" or the like does not necessarily limit the claim scope to a specific embodiment, and the reference to particularly preferred exemplary embodiments of the disclosure does not imply a limitation on the disclosure, and no such limitation is to be inferred. The disclosure is limited only by the spirit and scope of the appended claims. Moreover, these claims may refer to use "first", "second", etc. following with noun or element. Such terms should be understood as a nomenclature and should not be construed as giving the limitation on the number of the elements modified by such nomenclature unless specific number has been given. The abstract of the disclosure is provided to comply with the rules requiring an abstract, which will allow a searcher to quickly ascertain the subject matter of the technical disclosure of any patent issued from this disclosure. It is submitted with the understanding that it will not be used to interpret or limit the scope or meaning of the claims. Any advantages and benefits described may not apply to all embodiments of the disclosure. It should be appreciated that variations may be made in the embodiments described by persons skilled in the art without departing from the scope of the present disclosure as defined by the following claims. Moreover, no element and component in the present disclosure is intended to be dedicated to the public regardless of whether the element or component is explicitly recited in the following claims.

What is claimed is:

1. A use method of a drug scanning and identification system, comprising:
placing a first drug under test on a drug holder on a first spectrometer;
using a mobile device to issue a control command to trigger the first spectrometer scanning the first drug under test, so as to obtain first spectrum data of the first drug under test;
transmitting the first spectrum data of the first drug under test to the mobile device;
transmitting the first spectrum data of the first drug under test to a drug identification model; and
using the drug identification model to identify the first spectrum data of the first drug under test to generate an identification result, and displaying the identification result,
wherein the drug identification model is implemented to the mobile device or a cloud server,
wherein the drug identification model comprises a first level of identification model and a second level of identification model, the first level of identification model comprises a plurality of groups of drugs and a type of drug corresponding to each group in the plurality of groups of drugs, active pharmaceutical ingredients (API) and a dose ratio between the API and excipients, the second level of identification model comprises a dose ratio between a plurality of drugs and their corresponding API and the excipients in each group of drug categories.

2. A use method of a drug scanning and identification system, comprising:
placing a first drug under test on a drug holder on a first spectrometer;
using a mobile device to issue a control command to trigger the first spectrometer scanning the first drug under test, so as to obtain first spectrum data of the first drug under test;
transmitting the first spectrum data of the first drug under test to the mobile device;
transmitting the first spectrum data of the first drug under test to a drug identification model;
using the drug identification model to identify the first spectrum data of the first drug under test to generate an identification result, and displaying the identification result; and
using a plurality of spectrometers to establish a database, wherein the plurality of spectrometers comprise the first spectrometer and at least one second spectrometer, the first drug under test is placed on the drug holder of the first spectrometer, the first spectrometer scans the first drug under test to obtain the first spectrum data, at least one second drug under test is placed on a drug holder of the at least one second spectrometer, the at least one second spectrometer respectively scans the at least one second drug under test to obtain at least one second spectrum data of the at least one second drug under test, the first spectrum data and the at least one second spectrum data are calculated to establish a database having the first spectrum data of the first drug under test and the second spectrum data of the at least one second drug under test.

3. The use method of the drug scanning and identification system according to claim 2, wherein the first drug under test and the second drug under test are the same drug, the first spectrum data and the second spectrum data are interpolated, the first spectrum data and the second spectrum data are smoothed and equidistantly interpolated, so that spectra in the first spectrum data and the second spectrum data form consistent wavelength position information.

4. A use method of a drug scanning and identification system, comprising:
placing a first drug under test on a drug holder on a first spectrometer;
using a mobile device to issue a control command to trigger the first spectrometer scanning the first drug under test, so as to obtain first spectrum data of the first drug under test;
transmitting the first spectrum data of the first drug under test to the mobile device;

transmitting the first spectrum data of the first drug under test to a drug identification model; and using the drug identification model to identify the first spectrum data of the first drug under test to generate an identification result, and displaying the identification result, wherein the step of using the drug identification model to identify the first spectrum data of the first drug under test to obtain the identification result of the first drug under test and displaying the identification result further comprises: selecting a classification mode or a qualification mode through a menu interface of the mobile device.

5. The use method of the drug scanning and identification system according to claim 4, wherein when the classification mode is selected, spectrum data of a drug most similar to the first spectrum data of the first drug under test is searched in the drug identification model, and there is a minimum error value between the spectrum data of the most similar drug and the first spectrum data of the first drug under test, so as to obtain the identification result of the first drug under test, wherein the identification result is a drug name, a main ingredient, the content of the main ingredient, a drug manufacturer and the spectrum data.

6. The use method of the drug scanning and identification system according to claim 4, wherein when the qualification mode is selected, a name of a predetermined drug is input to find spectrum data of the predetermined drug, the drug identification model is adapted to compare the first spectrum data of the first drug under test and the spectrum data of the predetermined drug and find out whether they are consistent, if a comparison result is positive, the mobile device displays "matched", otherwise, if they are not consistent, the mobile device displays "not matched".

* * * * *